United States Patent
Al-Majnouni et al.

(10) Patent No.: US 12,012,376 B2
(45) Date of Patent: Jun. 18, 2024

(54) PROCESS OF PRODUCING LIGHT OLEFINS FROM ISOMERIZED STRAIGHT RUN NAPHTHA

(71) Applicant: SABIC Global Technologies B.V., Bergen op Zoom (NL)

(72) Inventors: Khalid A. Al-Majnouni, Riyadh (SA); Ahmad M. Al-Shehri, Riyadh (SA); Naif A. Aldalaan, Riyadh (SA); Debdut S. Roy, Bangalore (IN); Vidya Sagar Guggilla, Bangalore (IN); Nabil Alyasser, Brampton (CA); Ahmed Al-Zenaidi, Riyadh (SA); Wojciech Supronowicz, Riyadh (SA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 17/047,017

(22) PCT Filed: Apr. 11, 2019

(86) PCT No.: PCT/IB2019/052999
§ 371 (c)(1),
(2) Date: Oct. 12, 2020

(87) PCT Pub. No.: WO2019/211684
PCT Pub. Date: Nov. 7, 2019

(65) Prior Publication Data
US 2021/0147321 A1 May 20, 2021

Related U.S. Application Data

(60) Provisional application No. 62/664,906, filed on Apr. 30, 2018.

(51) Int. Cl.
C07C 5/27 (2006.01)
C07C 4/06 (2006.01)

(52) U.S. Cl.
CPC .............. C07C 5/2708 (2013.01); C07C 4/06 (2013.01); *C07C 2529/40* (2013.01)

(58) Field of Classification Search
CPC ...... C07C 5/2708; C07C 4/06; C07C 2529/40
See application file for complete search history.

(56) References Cited

U.S. PATENT DOCUMENTS

| | | | | |
|---|---|---|---|---|
| 2,387,508 | A * | 10/1945 | Goldsby | C10G 59/02 208/64 |
| 3,557,022 | A * | 1/1971 | Rausch et al. | C07C 5/2754 585/350 |
| 4,181,599 | A | 1/1980 | Miller et al. | |
| 4,830,728 | A | 5/1989 | Herbst et al. | |
| 5,905,181 | A | 5/1999 | Galperin | |
| 6,548,725 | B2 * | 4/2003 | Froment | B01J 29/061 585/653 |
| 7,875,755 | B2 | 1/2011 | Voskoboynikov | |
| 8,293,961 | B2 | 10/2012 | Choi et al. | |
| 8,324,441 | B2 | 12/2012 | Wegerer et al. | |
| 10,441,944 | B2 * | 10/2019 | Ravishankar | B01J 27/188 |
| 2001/0056217 | A1 | 12/2001 | Froment et al. | |
| 2004/0059173 | A1 | 3/2004 | Houzvicka et al. | |
| 2009/0099398 | A1 | 4/2009 | Wegerer et al. | |
| 2009/0143629 | A1 | 6/2009 | Voskoboynikov | |
| 2012/0074039 | A1 | 3/2012 | Gonzalez et al. | |
| 2014/0357914 | A1 | 12/2014 | Funk et al. | |
| 2017/0001180 | A1 | 1/2017 | Ravishankar et al. | |

FOREIGN PATENT DOCUMENTS

| | | |
|---|---|---|
| CN | 1402770 A | 3/2003 |
| CN | 101092324 A | 12/2007 |
| CN | 100554229 C | 10/2009 |
| EP | 0520100 B1 | 12/1992 |
| EP | 2660288 A1 | 11/2013 |
| EP | 3095843 A1 | 11/2016 |
| WO | WO2006098712 A1 | 9/2006 |
| WO | WO2009065898 A1 | 5/2009 |
| WO | WO2013016660 A1 | 1/2013 |
| WO | WO2017205083 A1 | 11/2017 |

OTHER PUBLICATIONS

International Search Report and Written Opinion from PCT/IB2019/052999 dated Jul. 16, 2019, 10 pages.

* cited by examiner

*Primary Examiner* — Thuan D Dang
(74) *Attorney, Agent, or Firm* — Norton Rose Fulbright US LLP

(57) ABSTRACT

Systems and methods of producing olefins via catalytic cracking are disclosed. Hydrocarbons of a naphtha stream are isomerized by converting straight chain Cn hydrocarbons to branched Cn hydrocarbons, thereby forming an isomerized naphtha stream. The isomerized naphtha stream is subsequently fed to a catalytic cracking unit such that the hydrocarbons of the isomerized naphtha stream form olefins. In the catalytic cracking process, the reaction temperature can be kept lower than 680° C., thereby increasing the reactivity and minimizing catalyst deactivation in the catalytic cracking process.

5 Claims, 3 Drawing Sheets

PROCESS OF PRODUCING LIGHT OLEFINS FROM ISOMERIZED STRAIGHT RUN NAPHTHA

CROSS REFERENCE TO RELATED APPLICATIONS

This application is a national phase application under 35 U.S.C. § 371 of International Application No. PCT/IB2019/052999 filed Apr. 11, 2019, which claims priority to U.S. Provisional Patent Application No. 62/664,906 filed Apr. 30, 2018. The entire contents of each of the above-referenced disclosures is specifically incorporated by reference herein without disclaimer.

FIELD OF INVENTION

The present invention generally relates to light olefin production processes. More specifically, the present invention relates to a process that includes catalytically cracking isomerized naphtha to produce light olefins.

BACKGROUND OF THE INVENTION

Light olefins, including $C_2$ to $C_4$ olefins, are building blocks for many chemical processes. Light olefins are used to produce polyethylene, polypropylene, ethylene oxide, ethylene chloride, propylene oxide, and acrylic acid, which, in turn, are used in a wide variety of industries such as the plastic processing, construction, textile, and automotive industries. As a result, market demand for light olefins has been growing in the last few decades. Although steam cracking of hydrocarbons is the most common method to produce light olefins, many other processes, including catalytic cracking of naphtha, have been utilized to meet the increasing market demand for light olefins.

In the catalytic cracking process, liquid hydrocarbon feedstock reacts over a catalyst and breaks down into lighter olefins and other byproducts under high temperature and high pressure conditions. However, there are a few drawbacks in the production of light olefins using conventional catalytic cracking processes. For example, when the feed for the catalytic cracking includes paraffinic hydrocarbons with FBP (final boiling point) less than 350° C., a reaction temperature has to be kept much higher than 600° C. and a residence time is kept short in order to achieve high selectivity and high yield of light olefins. Thus, the overall energy consumption for this process is relatively high. Additionally, high reaction temperatures often cause deactivation of the catalyst, which can drastically reduce the production efficiency and increase the production cost of light olefins. Therefore, improvements in this field are desired.

BRIEF SUMMARY OF THE INVENTION

A solution to at least some of the above-mentioned problems associated with the process of light olefin production via catalytic cracking of naphtha has been discovered. The solution resides in a method that integrates a naphtha isomerization process with a catalytic cracking process. This can be beneficial for lowering reaction temperature and minimizing the occurrence of catalyst deactivation. Notably, the method isomerizes straight chain hydrocarbons in naphtha to form branched hydrocarbons such that the reaction temperature required to catalytically crack the hydrocarbons is lowered. This leads to reduced energy consumption and minimized catalyst deactivation during the catalytic cracking process. Therefore, the methods of the present invention provide a technical advantage over at least some of the problems associated with the currently available methods for catalytic cracking naphtha mentioned above.

Embodiments of the invention include a method of producing olefins. The method comprises isomerizing hydrocarbons of a naphtha stream by converting straight chain $C_n$ hydrocarbons to branched $C_n$ hydrocarbons and thereby form an isomerized naphtha stream, and catalytic cracking of hydrocarbons of the isomerized naphtha stream to form olefins.

Embodiments of the invention include a method of producing olefins. The method comprises isomerizing hydrocarbons of a naphtha stream by converting straight chain $C_n$ hydrocarbons to branched $C_n$ hydrocarbons and thereby forming an isomerized naphtha stream. The isomerizing comprises contacting the naphtha stream with a catalyst at a temperature of 40 to 300° C. and pressure of 10 to 40 bars. The method further includes catalytic cracking of hydrocarbons of the isomerized naphtha stream to form olefins.

Embodiments of the invention include a method of producing olefins. The method includes flowing a naphtha stream to a fixed bed isomerization reactor. The method further includes isomerizing, in the fixed bed isomerization reactor, hydrocarbons of the naphtha stream by converting straight chain $C_n$ hydrocarbons to branched $C_n$ hydrocarbons and thereby forming an isomerized naphtha stream. The isomerizing comprises contacting the naphtha stream with a catalyst at a temperature of 40 to 300° C. and pressure of 10 to 40 bar. The method further includes heating hydrocarbons of the isomerized naphtha stream to a temperature in a range of 550 to 680° C. The method further still includes catalytic cracking, in a catalytic cracking reactor, the heated hydrocarbons of the isomerized naphtha stream to form olefins.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, light olefins can be produced by catalytic cracking of liquid naphtha at a reaction temperature higher than 600° C., which leads to high energy consumption and high catalyst deactivation rate during the catalytic cracking process. The present invention provides a solution to the problem. The solution is premised on a method that includes isomerizing straight chain hydrocarbons in naphtha prior to the catalytic cracking process. The isomerized naphtha hydrocarbons can be converted into light olefins via catalytic cracking at a much lower reaction temperature, thereby reducing energy consumption and minimizing catalyst deactivation during the olefin production process. These and other non-limiting aspects of the present invention are discussed in further detail in the following sections.

A. System for Producing Olefins

Figure 1:
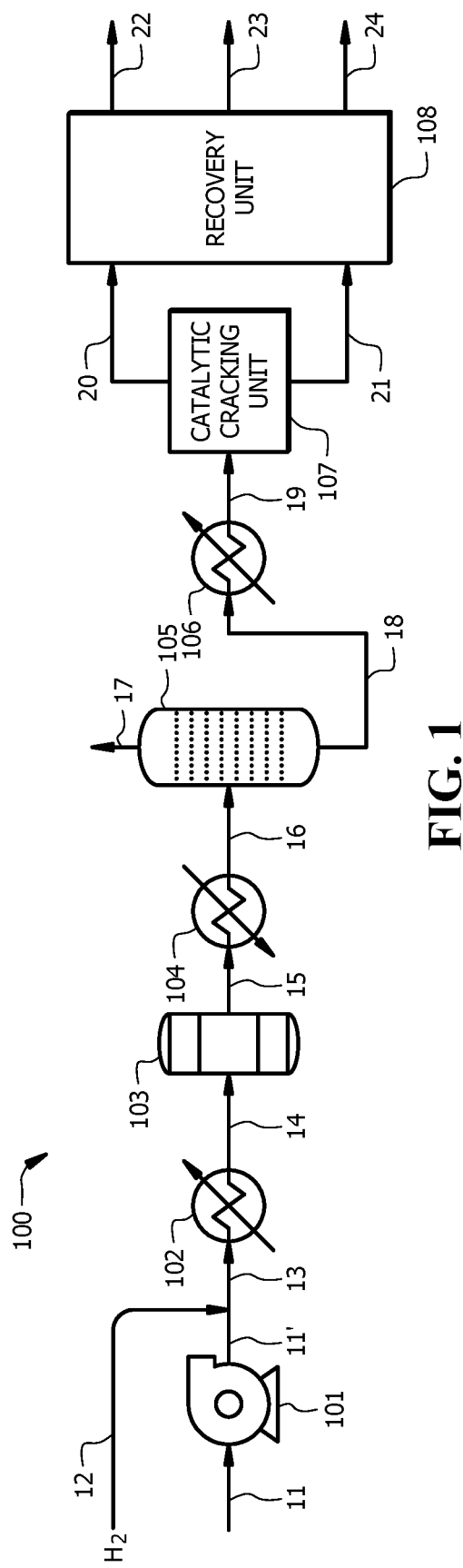
FIG. 1 shows a schematic diagram for a system for producing olefins, according to embodiments of the invention.

In embodiments of the invention, the system for producing olefins can include an integrated system of an isomerization unit and a catalytic cracking unit. With reference to FIG. 1, a schematic diagram is shown of olefin production system 100 that is capable of producing light olefins with lower reaction temperature in the catalytic cracking process than a conventional catalytic cracking process. According to embodiments of the invention, olefin production system 100 may include feed pump 101 configured to receive hydrocarbon feed stream 11. Feedstock stream 11' from feed pump 101 may be mixed with hydrogen stream 12 to form mixed feed stream 13. An outlet of feed pump 101 may be in fluid communication with first pre-heater 102. In embodiments of the invention, first pre-heater 102 may be configured to heat mixed feed stream 13 to produce heated feed stream 14. Depending on the catalyst used, heated feed stream 14 may be at a temperature of 80 to 250° C. and all ranges and values there between including ranges of 80 to 90° C., 90 to 100° C., 100 to 110° C., 110 to 120° C., 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., and 240 to 250° C.

In embodiments of the invention, an outlet of first pre-heater 102 may be in fluid communication with isomerization reactor 103. Isomerization reactor 103 may be configured to isomerize straight chain hydrocarbons from heated feed stream 14 to form isomerized feed stream 15 comprising branched hydrocarbons. According to embodiments of the invention, isomerization reactor 103 may be a fixed bed reactor containing a catalyst such as zeolite, chlorinated alumina, metal oxides, or combinations thereof.

In embodiments of the invention, an outlet of isomerization reactor 103 may be in fluid communication with cooler 104. In embodiments of the invention, cooler 104 may be configured to cool isomerized feed stream 15 to form cooled isomerized stream 16. Cooler 104 may include a heat exchanger, fin fan, or combinations thereof. According to embodiments of the invention, an outlet of cooler 104 may be in fluid communication with separation column 105 such that cooled isomerized stream 16 flows from cooler 104 to separation column 105. In embodiments of the invention, separation column 105 may be configured to separate $H_2$ and light gases such as methane and ethane that are formed during the isomerization reactions from cooled isomerized stream 16 and form stream 17 containing primarily $H_2$ and light gases and cracking unit feed stream 18. According to embodiments of the invention, separation column 105 may include one or more distillation columns, separators, or combinations thereof.

In embodiments of the invention, an outlet of separation equipment 105 may be in fluid communication with second pre-heater 106 such that cracking unit feed stream 18 flows from separation equipment 105 to second pre-heater 106. Second pre-heater 106 may be configured to heat cracking unit feed stream 18 to form heated cracking unit feed stream 19. In embodiments of the invention, cracking unit feed stream 18 may be heated to a temperature in a range of 500 to 680° C. and all ranges and values there between including ranges of 500 to 505° C., 505 to 510° C., 510 to 515° C., 515 to 520° C., 520 to 525° C., 525 to 530° C., 530 to 535° C., 535 to 540° C., 550 to 545° C., 545 to 550° C., 550 to 555° C., 555 to 560° C., 560 to 565° C., 565 to 570° C., 570 to 575° C., 575 to 580° C., 580 to 585° C., 585 to 590° C., 590 to 595° C., 595 to 600° C., 600 to 605° C., 605 to 610° C., 610 to 615° C., 615 to 620° C., 620 to 625° C., 625 to 630° C., 630 to 635° C., 635 to 640° C., 640 to 645° C., 645 to 650° C., 650 to 655° C., 655 to 660° C., 660 to 665° C., 665 to 670° C., 670 to 675° C., and 675 to 680° C.

According to embodiments of the invention, an outlet of second pre-heater 106 may be in fluid communication with catalytic cracking unit 107 such that heated cracking unit feed stream 19 flows from second pre-heater 106 to catalytic cracking unit 107. In embodiments of the invention, catalytic cracking unit 107 may include one or more fixed bed reactors, one or more moving bed reactors, one or more fluidized bed reactors, or combinations thereof. A catalyst in catalytic cracking unit 107 may include ZSM-5, zeolite Y, Beta and metal or transition metals such as germanium, gallium, iron, or combinations thereof. According to embodiments of the invention, catalytic cracking unit 107 may be configured to convert hydrocarbons in heated cracking unit feed stream 19 to olefins. In embodiments of the invention, catalytic cracking unit 107 may be in fluid communication with recovery unit 108 adapted to separate effluent, including gas product stream 20 and liquid product stream 21, from catalytic cracking unit into light olefin stream 22, aromatic stream 23, and recycle stream 24 which contains $C_4$ to $C_6$ paraffins and olefins.

B. Method for Producing Light Olefins

Figure 2:
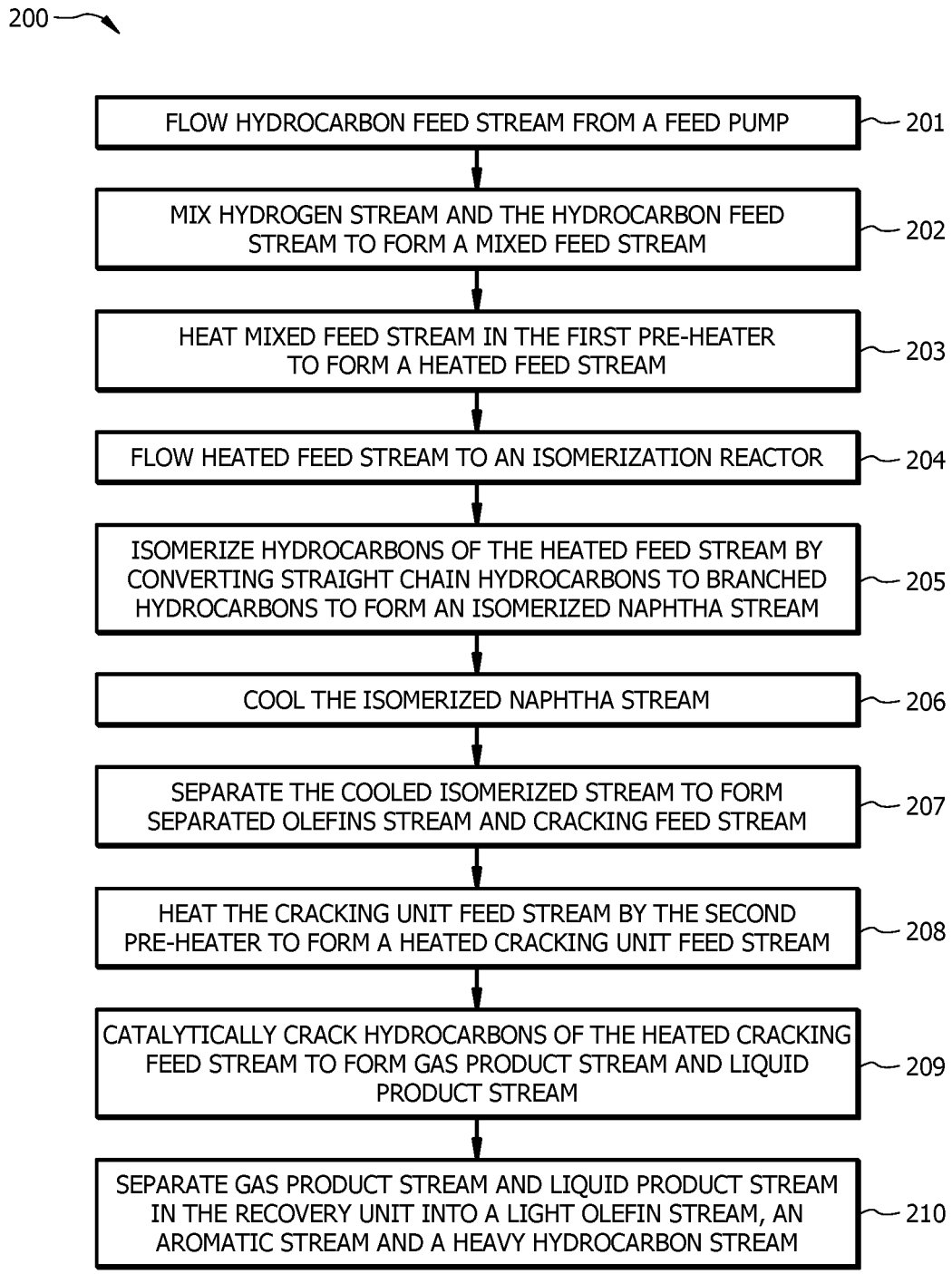
FIG. 2 shows a schematic flow chart for a method of producing olefins, according to embodiments of the invention.

As shown in FIG. 2, embodiments of the invention include method 200 for producing light olefins. Method 200 may be implemented by olefin production system 100 as shown in FIG. 1. According to embodiments of the invention, method 200, as implemented by olefin production system 100, may include flowing hydrocarbon feed stream 11 from feed pump 101, as shown in block 201. In embodiments of the invention, hydrocarbon feed stream 11 may be a naphtha stream. The naphtha stream may include straight run light naphtha and/or heavy naphtha.

According to embodiments of the invention, method 200 may include mixing hydrogen stream 12 with hydrocarbon feed stream 11 to form mixed feed stream 13, as shown in block 202. In embodiments of the invention, mixed feed stream 13 may include 0.1 to 4 molar ratio of hydrogen to hydrocarbons and all values and ranges there between including 0.1 to 0.2, 0.2 to 0.4, 0.4 to 0.6, 0.6 to 0.8, 0.8 to 1.0, 1.0 to 1.2, 1.2 to 1.4, 1.4 to 1.6, 1.6 to 1.8, 1.8 to 2.0, 2.0 to 2.2, 2.2 to 2.4, 2.4 to 2.6, 2.6 to 2.8, 2.8 to 3.0, 3.0 to 3.2, 3.2 to 3.4, 3.4 to 3.6, 3.6 to 3.8, and 3.8 to 4.0. In embodiments of the invention, method 200 may further include heating mixed feed stream 13 by first pre-heater 102 to form heated feed stream 14, as shown in block 203. Mixed feed stream 13 may be heated to a temperature in a range of 80 to 250° C. and all ranges and values there between, including 80 to 90° C., 90 to 100° C., 100 to 110° C., 110 to 120° C., 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., and 240 to 250° C.

According to embodiments of the invention, method 200 may include flowing heated feed stream 14 (including naphtha and hydrogen) to isomerization reactor 103, as shown in block 204. Isomerization reactor 103 may include one or more fixed bed reactors. Method 200 may further include isomerizing, in isomerization reactor 103, hydrocarbons of heated feed stream 14 by converting straight chain $C_n$ hydrocarbons to branched $C_n$ hydrocarbons, and thereby form isomerized feed stream 15, as shown in block 205. In embodiments of the invention, the $C_n$ hydrocarbons include $C_4$, $C_5$, $C_6$, $C_7$, $C_8$ hydrocarbons and combinations thereof. In embodiments of the invention, a catalyst in isomerization reactor 103 may include zeolite, chlorinated alumina, metal oxides, or combinations thereof.

According to embodiments of the invention, the isomerizing at block 205 may be performed at a temperature of 40 to 300° C. and all ranges and values there between, including ranges of 40 to 60° C., 60 to 80° C., 80 to 100° C., 100 to 120° C., 120 to 140° C., 140 to 160° C., 160 to 180° C., 180 to 200° C., 200 to 220° C., 220 to 240° C., 240 to 260° C., 260 to 280° C., and 280 to 300° C. The isomerizing in block 205 may be performed at a pressure of 10 to 40 bar and all ranges and values there between including ranges of 10 to 12 bar, 12 to 14 bar, 14 to 16 bar, 16 to 18 bar, 18 to 20 bar, 20 to 22 bar, 22 to 24 bar, 24 to 26 bar, 26 to 28 bar, 28 to 30 bar, 30 to 32 bar, 32 to 34 bar, 34 to 36 bar, 36 to 38 bar, and 38 to 40 bar. In embodiments of the invention, a liquid hourly space velocity for the isomerizing in block 205 may be in a range of 0.5 to 5 $hr^{-1}$ and all ranges and values there between including ranges of 0.5 to 0.8 $hr^{-1}$, 0.8 to 1.1 $hr^{-1}$, 1.1 to 1.4 $h^{-1}$, 1.4 to 1.7 $hr^{-1}$, 1.7 to 2.0 $h^{-1}$, 2.0 to 2.3 $hr^{-1}$, 2.3 to 2.6 $hr^{-1}$, 2.6 to 2.9 $hr^{-1}$, 2.9 to 3.2 $hr^{-1}$, 3.2 to 3.5 $hr^{-1}$, 3.5 to 3.8 $h^{-1}$, 3.8 to 4.1 $hr^{-1}$, 4.1 to 4.4 $hr^{-1}$, 4.4 to 4.7 $hr^{-1}$, and 4.7 to 5.0 $hr^{-1}$.

According to embodiments of the invention, isomerized feed stream 15 may be cooled by cooler 104 to form cooled isomerized stream 16, as shown in block 206. In embodiments of the invention, cooled isomerized stream 16 may be at a temperature of 15 to 50° C. and all ranges and values there between including ranges of 15 to 17° C., 17 to 20° C., 20 to 23° C., 23 to 26° C., 26 to 29° C., 29 to 32° C., 32 to 35° C., 35 to 38° C., 38 to 41° C., 41 to 44° C., 44 to 47° C., and 47 to 50° C. In embodiments of the invention, as shown in block 207, cooled isomerized stream 16 is separated by separation column 105 to form separated olefins stream 17 and cracking unit feed stream 18. Separated olefins stream 17 may include $C_2$ and $C_3$ olefins. In embodiments of the invention, cracking unit feed stream 18 may be heated by second pre-heater 106 to form heated cracking unit feed stream 19, as shown in block 208. According to embodiments of the invention, cracking unit feed stream 18 is heated to a temperature of 550 to 680° C. and all ranges and values there between, including ranges of 550 to 560° C., 560 to 570° C., 570 to 580° C., 580 to 590° C., 590 to 600° C., 600 to 610° C., 610 to 620° C., 620 to 630° C., 630 to 640° C., 640 to 650° C., 650 to 660° C., 660 to 670° C., and 670 to 680° C.

According to embodiments of the invention, as shown in block 209, method 200 may include catalytic cracking of hydrocarbons of heated cracking unit feed stream 19 (from isomerized feed stream 15) to form gas product stream 20 and liquid product stream 21. At block 209, hydrocarbons of heated cracking unit feed stream 19 may be converted to olefins. In embodiments of the invention, catalytic cracking at block 209 is performed in catalytic cracking unit 107. Catalytic cracking unit 107 may comprise one or more catalytic cracking reactors. In embodiments of the invention, the catalytic cracking reactor may include a fixed bed reactor, a moving bed reactor, or a fluidized bed reactor. The catalytic cracking reactor may include a catalyst comprising ZSM-5, Zeolite Y, germanium, gallium, iron, or combinations thereof. In embodiments of the invention, the reaction conditions for catalytic cracking at block 209 may include a reaction temperature of 600 to 720° C. and all ranges and values there between, including 600 to 610° C., 610 to 620° C., 620 to 630° C., 630 to 640° C., 640 to 650° C., 650 to 660° C., 660 to 670° C., 670 to 680° C., 680 to 690° C., 690 to 700° C., 700 to 710° C., and 710 to 720° C. The reaction conditions for catalytic cracking at block 209 may further include a reaction pressure of 1 to 5 bar and all ranges and values there between including ranges of 1 to 1.2 bar, 1.2 to 1.4 bar, 1.4 to 1.6 bar, 1.6 to 1.8 bar, 1.8 to 2.0 bar, 2.0 to 2.2 bar, 2.2 to 2.4 bar, 2.4 to 2.6 bar, 2.6 to 2.8 bar, 2.8 to 3.0 bar, 3.0 to 3.2 bar, 3.2 to 3.4 bar, 3.4 to 3.6 bar, 3.6 to 3.8 bar, 3.8 to 4.0 bar, 4.0 to 4.2 bar, 4.2 to 4.4 bar, 4.4 to 4.6 bar, 4.6 to 4.8 bar, and 4.8 to 5.0 bar. In embodiments of the invention, catalytic cracking is performed in a fixed catalyst bed and the reaction conditions may further include a weight hourly space velocity in a range of 1 to 20 h$^{-1}$ and all ranges and values there between including 2 hr$^{-1}$, 3 hr$^{-1}$, 4 hr$^{-1}$, 5 hr$^{-1}$, 6 hr$^{-1}$, 7 hr$^{-1}$, 8 hr$^{-1}$, 9 hr$^{-1}$, 10 hr$^{-1}$, 11 hr$^{-1}$, 12 hr$^{-1}$, 13 hr$^{-1}$, 14 hr$^{-1}$, 15 hr$^{-1}$, 16 hr$^{-1}$, 17 hr$^{-1}$, 18 hr$^{-1}$, and 19 hr$^{-1}$. Alternatively or additionally, catalytic cracking may be performed in a fluidized catalyst bed and the reaction conditions may further include a catalyst to oil ratio of 5 to 60 by weight and all ranges and values there between including ranges of 5 to 10, 10 to 15, 15 to 20, 20 to 25, 25 to 30, 30 to 35, 35 to 40, 40 to 45, 45 to 50, 50 to 55, and 55 to 60.

In embodiments of the invention, as shown in block 210, method 200 may include separating gas product stream 20 and liquid product stream 21 in recovery unit 108 into light olefin stream 22, aromatic stream 23 and heavy hydrocarbon stream 24. In embodiments of the invention, light olefin stream 22 may include 10 to 35 vol. % ethylene, and 10 to 35 vol. % propylene. Aromatics stream 23 may include about 20 mol. % of benzene, about 30 mol. % of toluene, and about 20 mol. % of xylenes. In embodiments of the invention, paraffins and heavy olefins (C$_4$ to C$_6$ olefins) in stream 24 (recycle stream) may be recycled back to catalytic cracking unit 107.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Example 1

Comparison of Catalytic Cracking Products from n-Hexane and Iso-Hexane

N-hexane and iso-hexane were each individually used as feed stock for a catalytic cracking process. ZSM-5 was used as the catalyst in the catalytic cracking process. The reaction temperature was 600° C. The reaction pressure was kept at 3 bar. The weight hourly space velocity was 40 hr$^{-1}$ for the catalytic cracking process. No steam was used for the catalytic cracking process. The product streams from the catalytic cracking process were analyzed. For each component in the product stream, the difference in yields between using n-hexane as feed and using iso-hexane as feed was calculated and shown in Table 1.

| component | Yields (wt. %) iso-Hexane - n-Hexane |
|---|---|
| Methane | 3 |
| Ethane | −3 |
| Ethylene | 0.5 |
| propane | −8 |
| propylene | 4.5 |
| butane | −2.5 |
| butenes | 4 |
| Light olefins | 9 |

As shown in Table 1, the yield of propylene increased by 4.5 wt. % and the yield of ethylene increased by 0.5 wt. % when using iso-hexane as feed compared to using n-hexane as feed. Therefore, the results indicate that branched hydrocarbons (e.g., iso-hexane) had a higher yield for light olefins in a catalytic cracking process.

Example 2

Comparison of Catalytic Cracking Products from Branched C$_6$ Hydrocarbons

Figure 3:
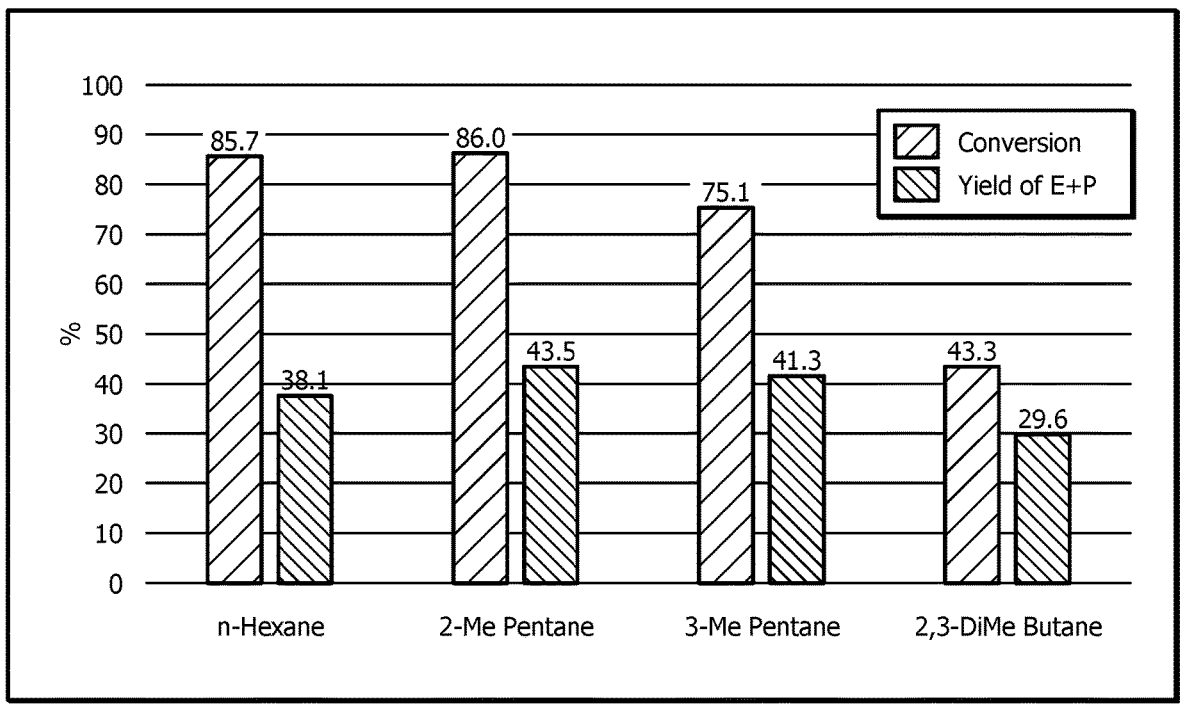
FIG. 3 is a bar chart showing conversion rates of $C_6$ hydrocarbons and yield of ethylene and propylene from the $C_6$ hydrocarbons in a catalytic cracking process, according to embodiments of the invention.

Streams of n-hexane, 2-methyl pentane, 3-methyl pentane and 2,3-dimethyl butane were each individually used as feedstock for a catalytic cracking process. In the catalytic cracking process, ZSM-5 was used as the catalyst. Reaction conditions included a reaction temperature of 600° C., a steam to hydrocarbon ratio of 1:2 and a weight hourly space velocity of 7.5 hr$^{-1}$. The conversion rate and yield to ethylene and propylene (E+P) for each feedstock are shown in FIG. 3. The results in FIG. 3 showed that mono-branched C$_6$ hydrocarbons had the highest conversion rate to ethylene and propylene. Specifically, 2-methyl pentane had the highest conversion rate of 86.0% and an ethylene and propylene yield of 43.5%. 3-methyl pentane had the second highest yield of ethylene and propylene. The overall results indicate isomerizing hydrocarbons (from straight-chain to branched hydrocarbons) can increase the yield of light olefins in the catalytic cracking process.

In the context of the present invention, embodiments 1-18 are described. Embodiment 1 is a method of producing olefins. The method includes isomerizing hydrocarbons of a naphtha stream by converting straight chain C$_n$ hydrocarbons to branched C$_n$ hydrocarbons and thereby form an isomerized naphtha stream, and catalytic cracking of hydrocarbons of the isomerized naphtha stream to form olefins. Embodiment 2 is the method of embodiment 1, wherein the isomerizing includes contacting the naphtha stream with a catalyst at a temperature of 40 to 300° C. and pressure of 10 to 40 bars. Embodiment 3 is the method of embodiment 2, wherein the catalyst for the isomerizing step is selected from the group consisting of zeolite based catalyst, chlorinated alumina based catalyst, metal oxides based catalyst, and combinations thereof. Embodiment 4 is the method of any of embodiments 1 to 3, further including separating the isomerized naphtha stream to remove light gases including H$_2$, methane, and ethane. Embodiment 5 is the method of embodiment 4, wherein the separating is performed in a separation equipment. Embodiment 6 is the method of any of embodiments 1 to 5, further comprising heating hydrocarbons of the isomerized naphtha stream prior to the catalytic cracking step. Embodiment 7 is the method of embodiment 6, wherein the hydrocarbons of the isomerized naphtha stream are heated to a temperature in a range of 500 to 680° C. Embodiment 8 is the method of any of embodiments 1 to 7, wherein the naphtha stream comprises straight run light naphtha and/or heavy naphtha. Embodiment 9 is the method of any of embodiments 1 to 8, further including adding hydrogen to the naphtha stream prior to the isomerizing step. Embodiment 10 is the method of any of embodiments 1 to 9, wherein the $C_n$ hydrocarbons include $C_4$, $C_5$, $C_6$, $C_7$, $C_8$ hydrocarbons, or combinations thereof. Embodiment 11 is the method of any of embodiments 1 to 10, wherein the naphtha stream is pre-heated to a temperature of 80 to 250° C. prior to isomerizing. Embodiment 12 is the method of any of embodiments 1 to 11, wherein the catalytic cracking is performed in a catalytic cracking reactor selected from the group consisting of a fixed bed reactor, a moving bed reactor, and a fluidized bed reactor. Embodiment 13 is the method of embodiment 12, wherein the catalytic cracking is performed in a fixed catalyst bed with a weight hourly space velocity in a range of 1 to 20 $hr^{-1}$. Embodiment 14 is the method of embodiment 12, wherein the catalytic cracking is performed in a fluidized bed with a catalyst to oil ratio of 5 to 60 by weight in the case of fluidized bed reactor. Embodiment 15 is the method of any of embodiments 1 to 14, wherein the catalytic cracking is performed over a catalyst including ZSM-5, Zeolite Y, germanium, gallium, iron or combinations thereof. Embodiment 16 is the method of any of embodiments 1 to 15, wherein the catalytic cracking is performed under a reaction temperature of 600 to 700° C. Embodiment 17 is the method of any of embodiments 1 to 16, wherein the catalytic cracking is performed under a reaction pressure of 1 to 5 bar.

Embodiment 18 is a method of producing olefins. The method includes flowing a naphtha stream to a fixed bed isomerization reactor. The method also includes isomerizing, in the fixed bed isomerization reactor, hydrocarbons of the naphtha stream by converting straight chain $C_n$ hydrocarbons to branched $C_n$ hydrocarbons and thereby form an isomerized naphtha stream, wherein the isomerizing comprises contacting the naphtha stream with a catalyst at a temperature of 40 to 300° C. and pressure of 10 to 40 bar. The method further includes heating hydrocarbons of the isomerized naphtha stream to a temperature in a range of 500 to 680° C. The method also includes catalytic cracking, in a catalytic cracking reactor, the heated hydrocarbons of the isomerized naphtha stream to form olefins.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing olefins, the method comprising:
isomerizing hydrocarbons of a naphtha stream by converting straight chain $C_n$ hydrocarbons to branched $C_n$ hydrocarbons and thereby form an isomerized naphtha stream;
catalytically cracking hydrocarbons of the isomerized naphtha stream to form olefins;
separating the isomerized naphtha stream to remove light gases including $H_2$, methane, and ethane;
adding hydrogen to the naphtha stream prior to the isomerizing step;
heating hydrocarbons of the isomerized naphtha stream prior to the catalytic cracking step;
wherein the naphtha stream comprises straight run light naphtha and/or heavy naphtha;
wherein the catalyst for the isomerizing step is a chlorinated alumina-based catalyst;
wherein the isomerizing comprises contacting the naphtha stream with a catalyst at a temperature of 220 to 300° C. and pressure of 10 to 40 bars;
wherein the catalytic cracking is performed in a fixed catalyst bed reactor at a weight hourly space velocity in a range of 1 to 20 $hr^{-1}$;
wherein the catalytic cracking is performed over a catalyst including Zeolite Y, and a metal including germanium, gallium, iron or combinations thereof;
wherein the naphtha stream is pre-heated to a temperature of 80 to 250° C. prior to isomerizing;
wherein the isomerizing is conducted in a fixed bed isomerization reactor; and
further comprising heating hydrocarbons of the isomerized naphtha stream to a temperature in a range of 500 to 680° C. prior to the catalytic cracking step.

2. The method of claim 1, wherein the $C_n$ hydrocarbons include $C_4$, $C_5$, $C_6$, $C_7$, $C_8$ hydrocarbons, or combinations thereof.

3. The method of claim 1, wherein the naphtha stream is pre-heated to a temperature of 250° C. prior to isomerizing.

4. The method of claim 1, wherein the catalytic cracking is performed under a reaction temperature of 600 to 700° C.

5. The method of claim 1, wherein the catalytic cracking is performed under a reaction pressure of 1 to 5 bar.

* * * * *